United States Patent [19]
Taylor et al.

[11] Patent Number: 5,259,838
[45] Date of Patent: Nov. 9, 1993

[54] SYRINGE APPARATUS WITH ATTACHED PRESSURE GAUGE AND TIMER

[75] Inventors: Steven R. Taylor; Fred P. Lampropoulos, both of Salt Lake City; Thomas D. Stout, Sandy; A. Tony Smith, Salt Lake City, all of Utah

[73] Assignee: Merit Medical Systems, Inc., Salt Lake City, Utah

[21] Appl. No.: 900,987

[22] Filed: Jun. 18, 1992

[51] Int. Cl.⁵ .............................. A61M 29/00
[52] U.S. Cl. ......................... 604/97; 604/99
[58] Field of Search ................. 604/96–100, 604/208–211, 224

[56] References Cited

U.S. PATENT DOCUMENTS

| | | |
|---|---|---|
| 383,940 | 6/1888 | Brinkerhoff . |
| 404,105 | 5/1889 | Overlach . |
| 446,125 | 2/1891 | Schirmer . |
| 577,682 | 2/1897 | Eissner . |
| 730,054 | 6/1903 | Sheets . |
| 1,661,818 | 3/1928 | Cook . |
| 1,707,880 | 4/1929 | Sheets . |
| 2,656,836 | 10/1953 | Hickey ............... 128/215 |
| 2,672,866 | 3/1954 | Kater ................. 128/218 |
| 2,699,168 | 1/1955 | Lewis ................ 128/218 |
| 2,724,385 | 11/1955 | Lockhart ............ 128/261 |
| 2,736,315 | 2/1956 | Feeney ............... 128/218 |
| 2,764,978 | 10/1956 | Everett .............. 128/215 |
| 3,080,866 | 3/1963 | Friedman ........... 128/218 |
| 3,388,941 | 6/1968 | Marcus .............. 294/4 |
| 3,478,937 | 11/1969 | Solowey ............. 222/386 |
| 3,491,757 | 1/1970 | Arce .................. 128/221 |
| 3,529,596 | 9/1970 | Garner .............. 128/145.6 |
| 3,698,381 | 10/1972 | Federico et al. .... 128/1 R |
| 3,720,199 | 3/1973 | Rishton et al. ..... 128/1 D |
| 3,884,229 | 5/1975 | Raines et al. ...... 128/221 |
| 3,931,822 | 1/1976 | Marici ............... 128/351 |
| 3,966,358 | 6/1976 | Heimes et al. ..... 417/12 |
| 3,985,123 | 10/1976 | Herzlinger et al. .. 128/2.05 F |
| 3,992,926 | 11/1976 | Berryhill ........... 73/80 |
| 4,016,871 | 4/1977 | Schiff ............... 128/2.06 R |
| 4,057,050 | 11/1977 | Sarstedt ............ 128/2 F |
| 4,063,662 | 12/1977 | Drummond et al. .. 222/31 |
| 4,086,653 | 4/1978 | Gernes ............... 364/564 |
| 4,106,002 | 8/1978 | Hogue, Jr. ......... 340/626 |
| 4,182,344 | 1/1980 | Benson .............. 128/207.15 |
| 4,254,773 | 3/1981 | Waldbillig ......... 128/348 |
| 4,266,550 | 5/1981 | Bruner .............. 128/349 |
| 4,267,846 | 5/1981 | Kontos .............. 128/765 |

(List continued on next page.)

FOREIGN PATENT DOCUMENTS

| | | |
|---|---|---|
| 545415 | 8/1957 | Canada . |
| 0119296 | 9/1984 | European Pat. Off. . |
| 0149866 | 7/1985 | European Pat. Off. . |
| 0396353 | 11/1990 | European Pat. Off. . |
| 1242737 | 8/1960 | France . |
| WO92/17221 | 10/1992 | PCT Int'l Appl. . |
| 2083364A | 3/1982 | United Kingdom . |

OTHER PUBLICATIONS

"ACS Accessories Offer Optimum Efficiency in Your Angioplasty Procedures," Eli Lilly and Company.

(List continued on next page.)

*Primary Examiner*—John D. Yasko
*Assistant Examiner*—Anthony Gutowski
*Attorney, Agent, or Firm*—Workman, Nydegger, Jensen

[57] ABSTRACT

A syringe apparatus for use with balloon-tipped catheters is disclosed having an attached pressure gauge and timer assembly. In one mode, the timer assembly displays the duration of a current event of inflation or deflation, and the duration of the most recent past event of inflation or deflation. In another mode, the timer assembly displays historical information showing the event number and duration of past events of inflation and deflation. The pressure gauge display and the timer assembly display are situated conveniently on the syringe assembly and in proximity to one another so as to enable a syringe operator to substantially simultaneously monitor durations of inflation and deflation without the need for an assistant, yet without requiring purchase or use of computerized monitors.

18 Claims, 12 Drawing Sheets

SYRINGE APPARATUS WITH ATTACHED PRESSURE GAUGE AND TIMER

BACKGROUND OF THE INVENTION

1. Technical Field

The present invention relates to syringe devices used to inflate balloon-tipped catheters, such as coronary angioplasty dilatation catheters, and more particularly to a syringe apparatus having a pressure gauge mounted thereto.

2. Background Information

An important tool in present medical procedures is the use of balloon-tipped catheters. Numerous configurations of balloon-tipped catheters have been developed for particular medical procedures. For purposes of simplicity and brevity, the following discussion will be directed to the use of a particular type of balloon-tipped catheter generally known as coronary angioplasty dilatation catheters.

Following the first primitive experiments in coronary angioplasty in the 1970s, coronary angioplasty quickly received widespread attention as an alternative to coronary bypass surgery. Coronary bypass surgery involves surgical access to the heart, placing the patient on an extracorporeal blood oxygenation system so that the heart can be stopped for surgery, and then surgically attaching one or more passageways to bypass a clogged coronary artery, all under a general anesthetic. Coronary angioplasty, generally performed under a local anesthetic, involves running a dilatation catheter (a catheter having an inflatable balloon near the end) to the diseased blood vessel and then inflating the balloon in order to open the passageway, thereby obtaining increased blood flow. The angioplasty procedure typically involves less risk to the patient, and significantly lessens the patient's discomfort and recovery time.

Of great importance during an angioplasty procedure is to take notice that during inflation of the dilatation catheter, no blood can flow through the blood vessel being mechanically dilated. Clearly, the disruption of blood flow must be limited in duration so as to avoid tissue damage due to oxygen deprivation. Hence, it is important to insure that the balloon is deflated and blood flow restored before tissue damage can occur. In most cases, it is not possible to adequately dilate a diseased blood vessel in a single inflation. In cases where it is necessary to undertake multiple inflations in the same location it is important to allow sufficient time between successive inflations so that the tissues fed by the diseased blood vessel can become fully oxygenated before blood flow is disrupted again.

At the same time, it is important to the success of the procedure that the dilation of the vessel be permitted to extend for a significant period of time. Although specific techniques can vary significantly depending upon the nature of the blockage, the catheter being used, and the like, the most common technique involves inflating the catheter relatively rapidly and then leaving it in place for several minutes. Although it might be proposed to use very short intervals of inflation in order to minimize the risk due to oxygen deprivation, followed by long intervals of deflation, it has been found to be better to utilize very long intervals of inflation in order to achieve the most effective dilation of the diseased blood vessel, and short intervals of deflation in order to bring the procedure to a conclusion more rapidly. The typical angioplasty procedure compromises these two factors by maintaining the balloon in the inflated and deflated conditions for a moderate amount of time.

In order to insure the success of the procedure without damage to the tissues fed by the diseased blood vessel, it is critical to monitor the duration of each inflation and deflation. It is also important that the physician performing the angioplasty have access to historical information regarding the duration of past inflations and deflations. In the past, this information has typically been recorded manually. Commonly, the operator of the syringe used to apply the inflation pressure will call out as pressure is applied and the time is noted by an assistant, or the assistant activates a stopwatch. The assistant continuously monitors the time and informs the catheterization team as required. At the appropriate time, as determined by the directing physician, the syringe operator deflates the catheter while the assistant monitors the deflation time. The assistant also maintains a record of the duration of each inflation and deflation. At any given time, the directing physician can learn of the duration of the most recent inflation or deflation, and the history of past inflations and deflations by asking the assistant.

Obviously, this process is somewhat cumbersome, and is also subject to errors in computing durations, while recording the information, or reporting it as required. This is particularly so when the assistant has other significant duties. Yet, it is quite expensive to dedicate an assistant solely for the function of monitoring and recording times.

One approach to dispensing with the function of the assistant in monitoring times has been to utilize computers to serve that function. For example, one approach has been to incorporate a pressure transducer into the syringe system used to inflate the balloon-tipped catheter. A computer is then used to monitor the pressure transducer to mark changes in pressure corresponding to inflation and deflation, and the duration of each such pressure change. The difficulty with this approach is that although very accurate and reliable, it is expensive, and some angioplasty facilities are unable to afford to purchase one. This approach also involves the use of yet another instrument, and some directing physicians are unwilling to add another instrument to the already very cluttered angioplasty operating theater. Despite the serious shortcomings of the original system using an assistant to monitor and record times of inflation and deflation, facilities and physicians finding themselves unable or unwilling to add a computerized monitor have had no alternatives.

SUMMARY OF THE INVENTION

It is a primary object of the present invention to provide a syringe apparatus and attached pressure gauge and timing mechanism enabling a syringe operator to monitor inflation and deflation times without the need for an assistant, yet without requiring purchase or use of computerized monitors.

It is another object of the present invention to collect a record of inflation and deflation times which may be easily reviewed, without requiring an assistant to manually record such information.

Yet another object of the present invention is to provide a relatively low cost syringe apparatus capable of use by a single person to control and monitor inflation and deflation pressures and durations.

Additional objects and advantages of the invention are set forth hereinbelow in the detailed description, or will be appreciated by the practice of the invention.

To achieve the foregoing objects, and in accordance with the invention as embodied and broadly described herein, a syringe apparatus is provided which is adapted for use with balloon-tipped catheters. The syringe apparatus of the present invention is advantageously provided with a syringe assembly capable of generating pressures sufficient to inflate the balloon-tipped catheter, and also a pressure gauge and a timer assembly. In one mode, a presently preferred timer assembly displays the duration of a current event of inflation or deflation, and the duration of the most recent past event of inflation or deflation. In another mode, the timer assembly displays historical information showing the event number and duration of past events of inflation and deflation. The pressure gauge display and the timer assembly display are situated conveniently on the syringe assembly and in proximity to one another so as to enable a syringe operator to substantially simultaneously monitor durations of inflation and deflation without the need for an assistant, yet without requiring purchase or use of computerized monitors.

BRIEF DESCRIPTION OF THE DRAWINGS

In the accompanying drawings, which represent the best mode presently contemplated for carrying out the present invention.

DETAILED DESCRIPTION OF THE PREFERRED EMBODIMENT

The present invention is directed to a syringe apparatus having an attached pressure gauge and a timing mechanism which will enable a syringe operator to simultaneously monitor inflation and deflation pressures and durations of inflations and deflations.

Figure 1:
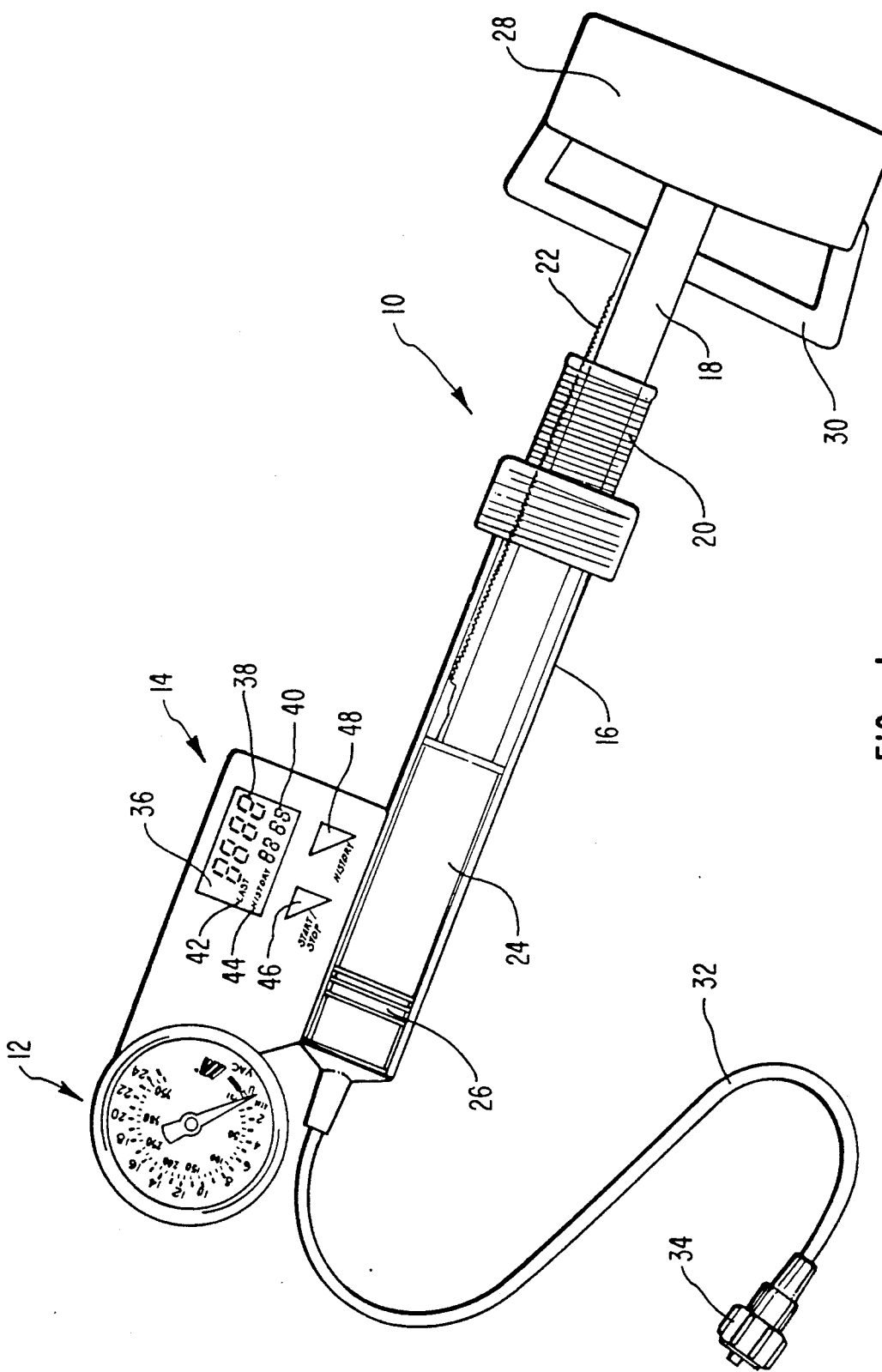
FIG. 1 is a perspective view of one presently preferred embodiment of a syringe apparatus in accordance with the present invention for use in inflating a balloon-tipped catheter.

Reference is first made to FIG. 1, which illustrates one presently preferred embodiment of a syringe apparatus constructed in accordance with the present invention. The syringe apparatus of FIG. 1 includes a syringe assembly, shown generally at reference numeral 10, a pressure gauge, shown generally at 12, and a timer assembly, shown generally at 14.

The syringe assembly is comprised of a syringe barrel 16 and a plunger 18. Syringe barrel 16 is preferably constructed of a clear polycarbonate, medical grade plastic material. Preferably, plunger 18 is also constructed of medical grade plastic material, though typically of an opaque nature.

Syringe barrel 16 is preferably provided with internal threads 20 adapted to engage with corresponding threads 22 on one side of plunger 18. Plunger 18 is slidably operative within syringe barrel 16. The distal end of plunger 18 is advantageously provided with a collar 24 fitted with a rubber tip 26 which provides a fluid-tight seal about the periphery of the barrel so that fluid can be expelled from the syringe barrel 16 through pressure tubing 32 and luer fitting 34 as plunger 18 is advanced into syringe barrel 16. During procedures involving a balloon-tipped catheter, luer fitting 34 is connected to the input end of such a catheter, so that fluid expelled from the syringe barrel 16 will inflate the balloon of the balloon-tipped catheter.

The proximal end of plunger 18 is preferably provided with a handle 28 and a trigger mechanism 30. Trigger mechanism 30 is connected to plunger threads 22, so that compression of trigger mechanism 30 towards handle 28 serves to disengage plunger threads 22 from engagement with barrel threads 20. When plunger threads 22 and barrel threads 20 are disengaged, plunger 18 is free to slide in or out of syringe barrel 16 through application of force by the operator of the syringe assembly. As soon as the operator releases trigger mechanism 30, plunger threads 22 will reengage barrel threads 20, thereby securing the plunger in position. Fine adjustments to the position of plunger 18 within syringe barrel 16 may be made by rotating the plunger clockwise or counterclockwise in a screwing motion. In this manner, fluid pressures can be quickly exerted and/or released as desired, but provision is also made for very precise adjustment of pressures by slowly screwing plunger 18 into or out of syringe barrel 16.

It is to be understood that the nature and mechanical aspects of the syringe assembly 10 are not limited to those specific features illustrated in FIG. 1, and that a variety of different types of syringe designs could be utilized without departing from the spirit and scope of the present invention. The particular syringe apparatus as illustrated in FIG. 1 is presently preferred, however. Its design is more particularly described in U.S. Pat. Nos. 5,047,015 and 5,057,078, both of which are incorporated herein by reference.

In the presently preferred embodiment illustrated in FIG. 1 and described herein, the timer assembly is adapted to perform two different functions: the first function being the display of the elapsed time of an ongoing inflation or deflation in real time while simultaneously displaying the total duration of the most recent preceding event of inflation or deflation; and the second function being the display of historical data of earlier events of inflation and deflation.

In order to present the information required in the performance of these two functions, timer assembly 14 is advantageously provided with a display 36 providing a visual readout of timer assembly data. Display 36 has two separate data readout areas, large numerals 38 and small numerals 40. As described more fully hereafter, large numerals 38 are used with respect to the first function to display the current duration of inflation and deflation in real time, and small numerals 40 are used to display the total duration of the most recent preceding event of inflation or deflation. With respect to the second, historical, function, large numerals 38 are used to depict the duration of a preceding event of inflation or deflation, and the small numerals 40 are used to identify which event is being displayed. For purposes of assisting the syringe operator to recognize which display is being viewed at any given moment, display 36 is also provided with two indicators: a "last" indicator 42, and a "history" indicator 44. "Last" indicator 42 is displayed during the timing of a current event, whereas "history" indicator 44 is displayed during the display of data relating to preceding events. Display 36 is preferably constructed from backlit liquid crystal display (LCD) components, although it will be appreciated that any display capable of running off of battery power could be substituted for LCDs.

The timer assembly is activated by use of an on/off switch (not shown), preferably located on the side of assembly 14. As described below, the initial operation of the on/off switch initializes timer assembly 14 and prepares it for timing of the first event in the inflation/deflation cycle of events. Activation of start/stop button 46 then initiates timing, and each succeeding activation of start/stop button 46 ends the timing of a current event, and commences timing of the next event. Timer assembly 14 is also provided with history button 48, used to access historical data. The provision of a start/stop button 46 and history button 48 lends the embodiment of FIG. 1 to being labeled a "2 button" embodiment.

Figure 2:
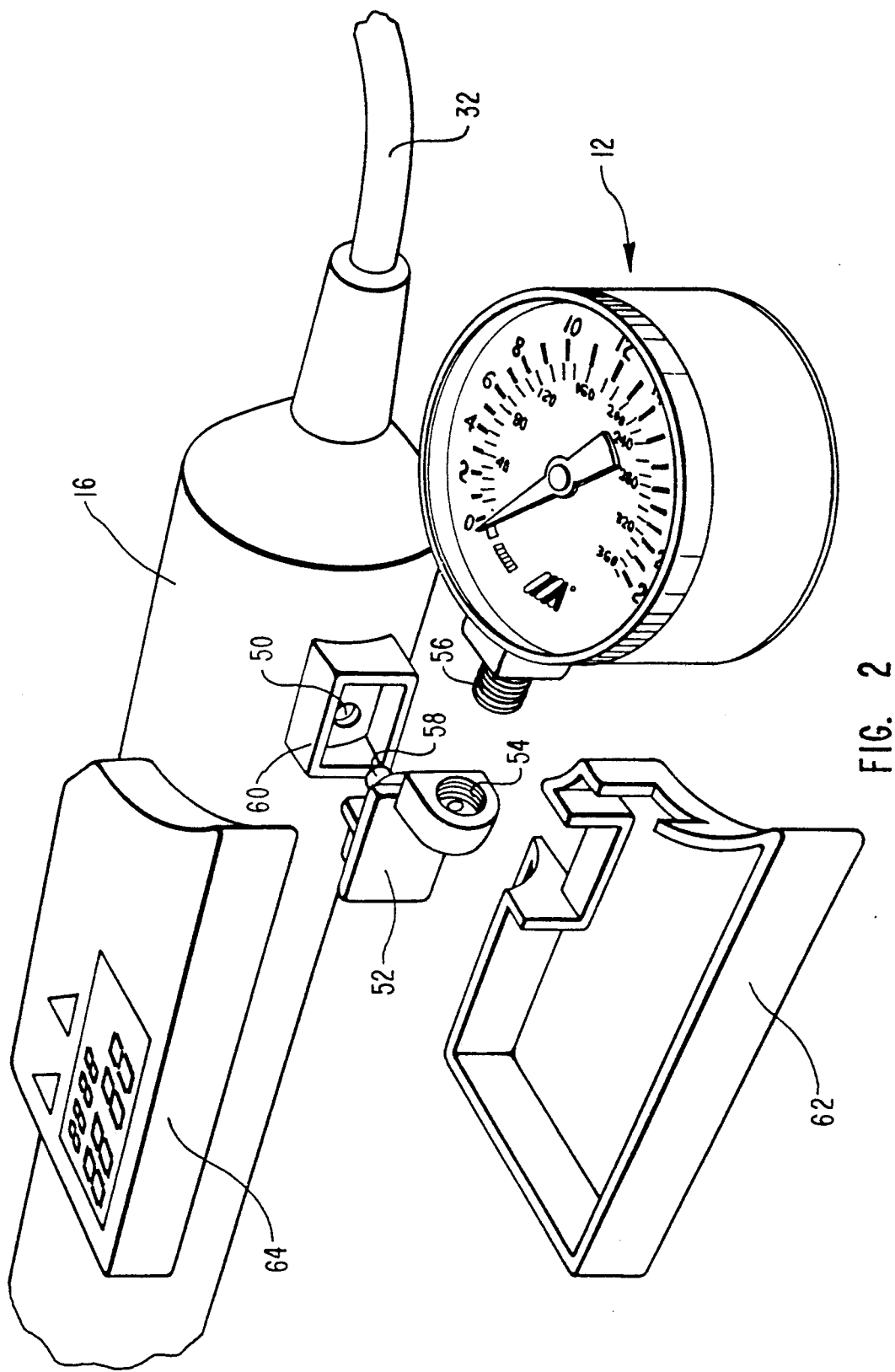
FIG. 2 is a partially exploded view of the syringe apparatus of FIG. 1, illustrating how the pressure gauge is interfaced to the syringe assembly in the presently preferred embodiment of the invention.

Referring now to FIG. 2, pressure gauge 12 of the presently preferred embodiment communicates with the interior of the syringe barrel 16 through a port 50. The pressure gauge 12 is coupled to port 50 through use of a fitting 52 having threads adapted for engagement with threads 56 of the pressure gauge in a fluid-tight manner. Fitting 52 is provided with a projection 58 adapted to mate with port 50. A housing well 60 attached to syringe barrel 16 or formed integrally therewith provides support to fitting 52 as well as to the bottom housing 62 and top housing 64 of the timer assembly. It will be appreciated that fitting 52 must be secured to port 50 in fluid-tight fashion, and that an appropriate adhesive should be used so as to insure the structural integrity of the syringe apparatus.

For use, the apparatus of the present invention is attached to a balloon-tipped catheter, such as an angioplasty catheter, in a conventional fashion. As soon as the directing physician calls for the first inflation, the syringe operator presses start/stop button 46 with his or her left thumb or other finger and then, after momentarily observing the timer assembly to insure it does not give out an error reading, advances plunger 18 within syringe barrel 16 with the operator's right hand while monitoring pressure gauge 12. An experienced syringe operator can easily and rapidly advance the plunger within the syringe barrel until the desired pressure is reached, thereby inflating the balloon the desired amount. It may be advantageous, however to provide markings (not shown) on the side of syringe barrel 16 to provide a reference for the syringe operator.

Figure 3:
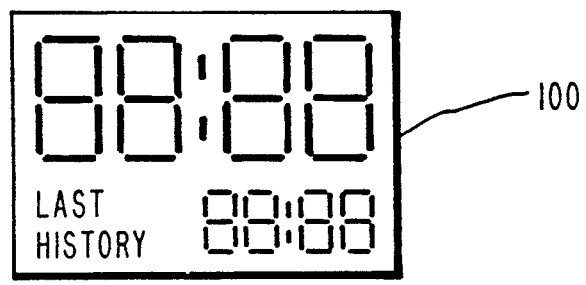
FIG. 3 is a series of views of the display used in connection with the timing of inflation and deflation events.
Figure 3:
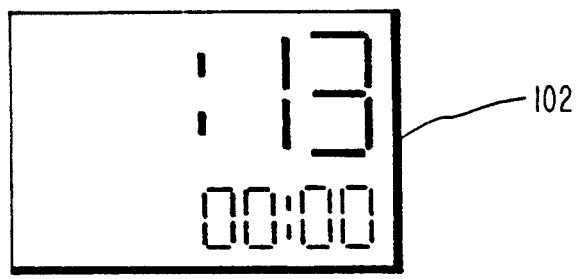
Figure 3:
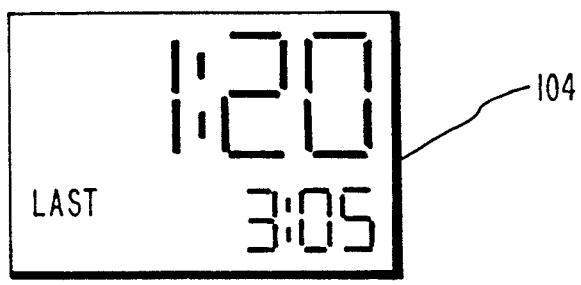
Figure 4:
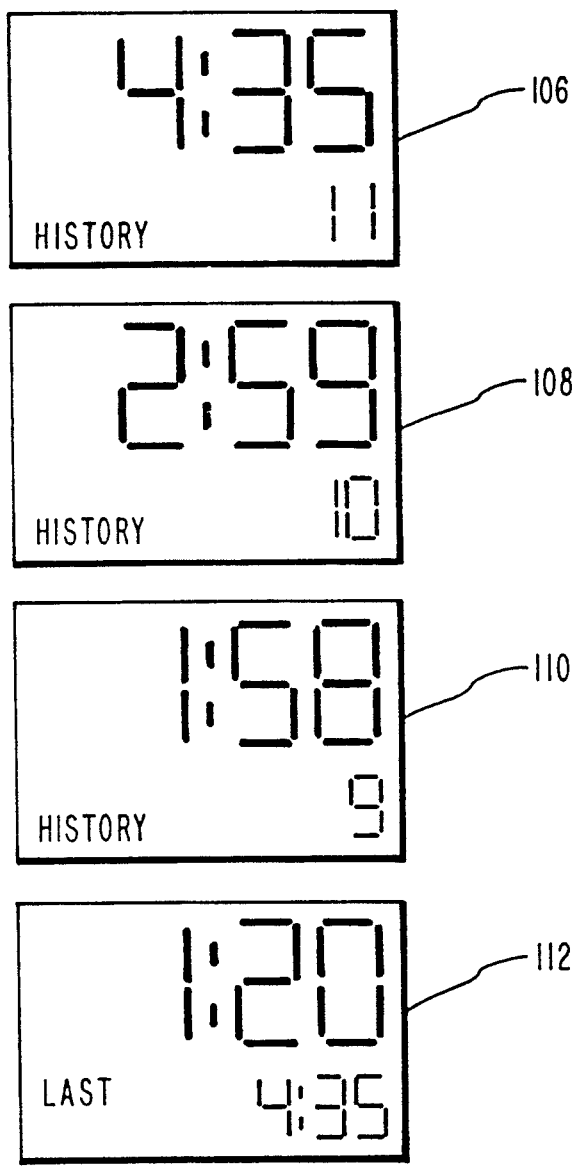
FIG. 4 is a series of views of the display used to present historical durations of various inflation and deflation events.

For purposes of discussion regarding the use and operation of the present invention, several events are illustrated in FIGS. 3 and 4. Each of these events depicts the display at a momentary instant of time during use of the invention, which for purposes of simplicity shall sometimes hereinafter be referred to as a "display condition."

With reference to FIG. 3, activation of the on/off switch causes initialization, observed as a momentary illumination of all segments of the liquid crystal display, shown generally as display condition 100. As soon as start/stop button 46 is activated, timer assembly 14 commences timing the first inflation event. Display condition 102 depicts the timer display 36 at a time 13 seconds after the start/stop button was first activated. Small numerals 40 will show a "zero" reading during the first inflation event, since there is no earlier event to report. At any given moment during this first inflation event, the directing physician may easily determine the duration of inflation by either asking the syringe operator or observing the timer assembly display himself or herself. Importantly, the syringe operator can monitor the time continuously without having to look away from the field of view directed at the pressure gauge.

At the appropriate time, which might be predetermined or might be determined from observations made during the course of a medical procedure involving a balloon-tipped catheter, the directing physician will instruct the syringe operator to commence deflation. Trigger mechanism 30 is retracted into handle 28, thereby disengaging plunger threads 22 from barrel threads 20, and the operator quickly retracts plunger 18 while restraining syringe barrel 16 in his or her other hand, thereby withdrawing fluid from the now-filled balloon at the tip of the balloon-tipped catheter, and thereby deflating the balloon. At about the same time, the operator activates start/stop button 46 to mark the end of the first event (inflation), and the commencement of the second event (deflation).

Display condition 104 depicts the situation one minute and 20 seconds after the start of the second event (deflation). It also depicts by the small LCD numerals the duration of the "last" event as having been 3 minutes 5 seconds. Hence, the syringe operator is able to monitor the current time of deflation and also observe the preceding duration of inflation.

of each succeeding event (inflation or deflation), the total duration of the immediately preceding event is displayed as the "last" event by the small LCD numerals, and the current duration of the current event is displayed by the large LCD numerals.

An additional feature of the "2 button" timer is the ability to review the "history" of past events (inflation and deflation). This feature is useful at the conclusion of the procedure in order to prepare a permanent record of the durations of inflations and deflations, and is also useful in circumstances where the directing physician has a question regarding previous inflation and/or deflation events.

The "history" function is accessed by activating history button 48. FIG. 4 depicts several display conditions which serve to illustrate the use of the history function of the presently preferred embodiment of the timer assembly of the present invention. Display condition 106 depicts a fictional reading which a syringe operator might observe during the course of an angioplasty procedure by pressing and holding down the history button. Display condition 106 shows that the immediately preceding event was event number 11, and that the duration of event number 11 was 4 minutes 35 seconds. While continuing to depress the history button 48, earlier events may be reviewed by repeatedly pressing the start/stop button 46. Display condition 108 depicts a fictional display after the syringe operator has pressed the start/stop button a single time. It shows that event number 10 had a duration of 2 minutes 59 seconds. Pressing start/stop button 46 again calls up the information stored for event number 9: display condition 110 shows that event number 9 had a duration of 1 minute 58 seconds. The durations of additional historical events may be accessed in similar fashion by additional activations of start/stop button 46, while continuing to depress history button 48.

The 2 button embodiment of timer assembly 14 does not display whether a current or historical event is an inflation or deflation. It is easy for one to read the data from the historical readout information, however, because inflations and deflations occur alternately, commencing with an inflation. Hence, in normal circumstances, each odd numbered event represents an inflation, and each even numbered event represents a deflation. It should be appreciated that a display indicating whether an event is an inflation or deflation could be added, wherein the label would alternate between "inflation" and "deflation" with each operation of the start/stop button.

As soon as the review of historical data is complete, the syringe operator releases history button 48. Display condition 112 illustrates that once this occurs, the timer assembly of the presently preferred embodiment reverts to tracking the current event and displaying the duration of the immediately preceding event. As shown in display condition 112, the current event has proceeded for 1 minute 20 seconds, and the last event had a duration of 4 minutes 35 seconds (which as noted in display condition 106, was event number 11).

From the foregoing, it will be appreciated that the 2 button syringe apparatus illustrated in FIGS. 1 and 2 solves the problems of conventional systems requiring either an additional assistant to monitor and record time information, or an expensive computer system. The syringe operator may easily and safely handle the task of timekeeping as well as controlling the syringe pressures and effecting the inflations and deflations of the balloon-tipped catheter.

Figure 5A:
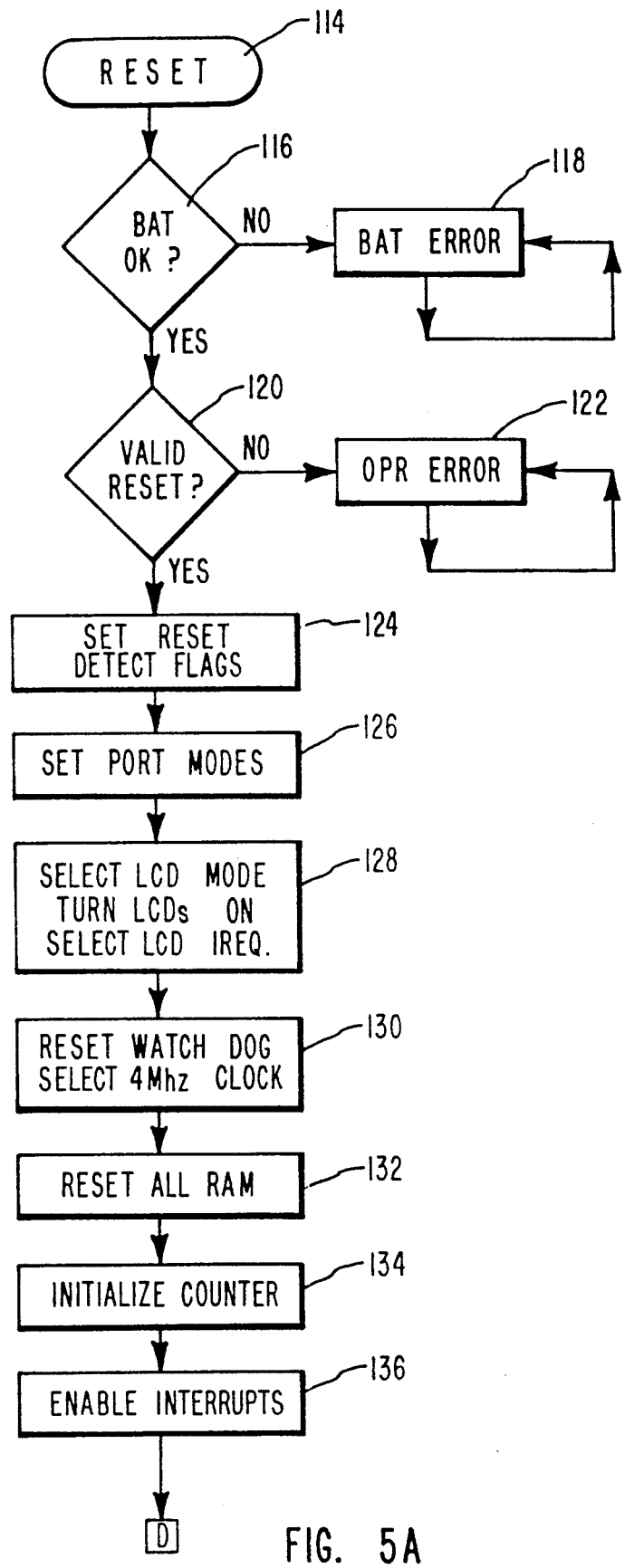
FIGS. 5A, 5B and 5C comprise a flow chart showing the flow of operations of the presently preferred timer assembly of the embodiment illustrated in FIG. 1.
Figure 5B:
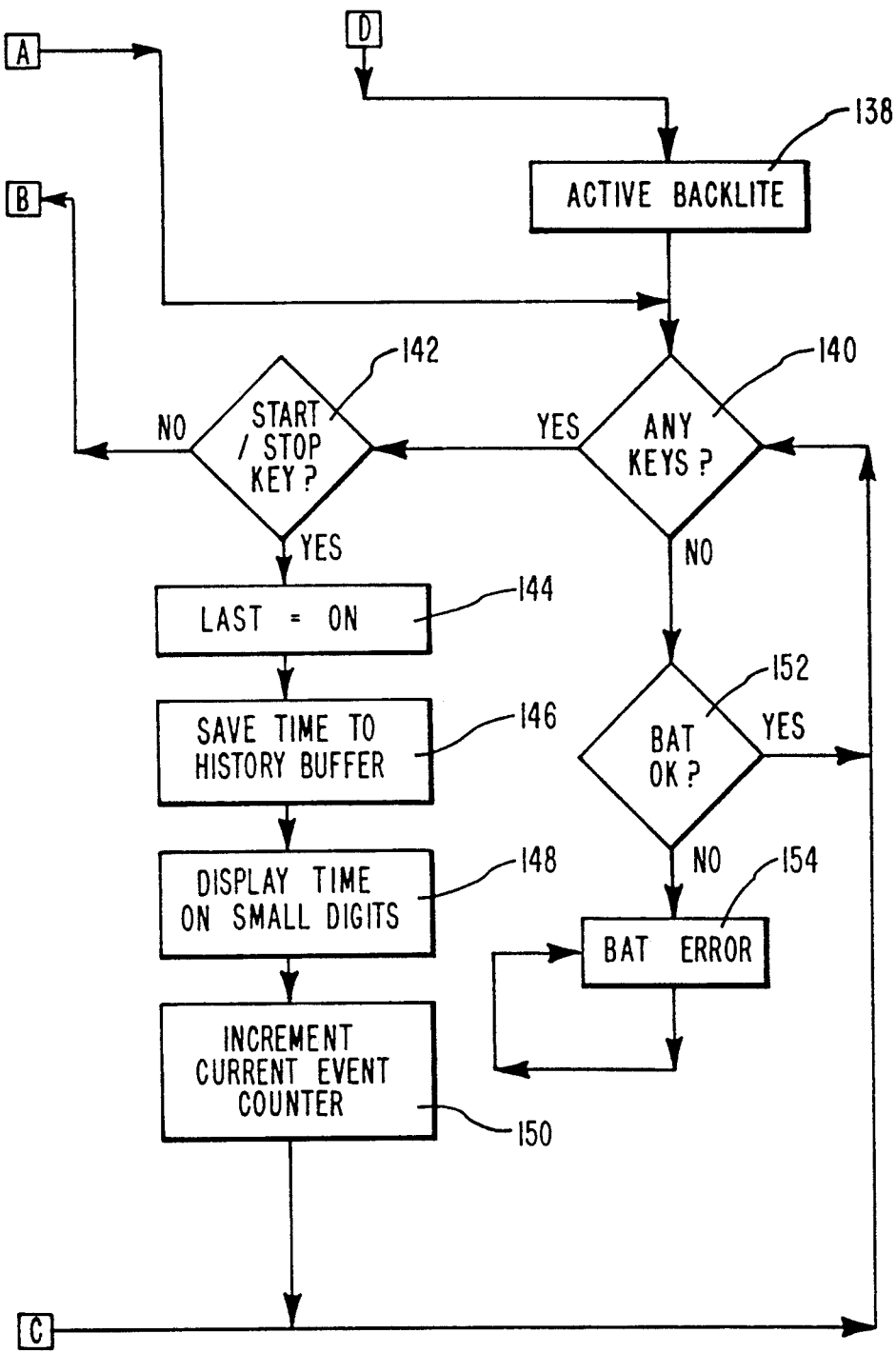
Figure 5C:
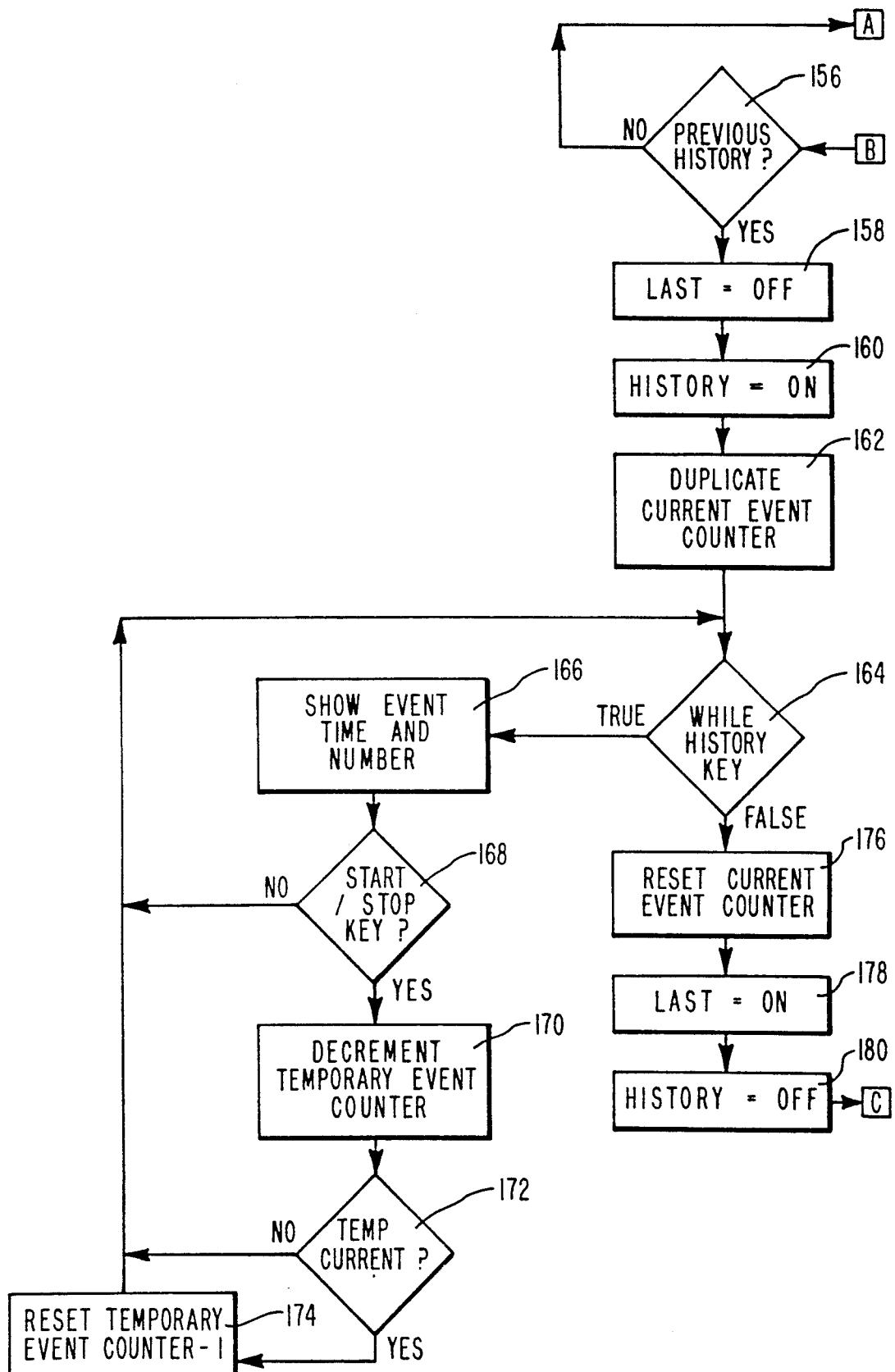

A flow chart of the presently preferred 2 button timer assembly 14 is illustrated in FIGS. 5A, 5B and 5C. Commencing with FIG. 5A, the flow of operations begins at step 114, depicted as "reset", which commences upon activation of the on/off switch at the commencement of the medical procedure involving the balloon-tipped catheter. The first step performed upon "reset" is testing the battery, shown at step 116. If not, a battery error condition 118 will prevent the timer assembly from operating. This is important because it would clearly be very disadvantageous for a battery to run down during an angioplasty or other balloon-tipped catheter procedure.

In the typical situation where the battery checks out satisfactorily, the next step 120 involves checking whether the reset was valid; if not, another error condition 122 is encountered, again preventing commencement of the medical procedure. Where the reset was valid, a series of steps quickly follow: a reset detect flag is set (step 124); port modes are set (step 126); the liquid crystal displays are activated (step 128); a Watch Dog is set, using a 4.19 megahertz clock (step 130); RAM memory is reset (step 132); the counter is reset (step 134); system interrupts are enabled (step 136); and the LCD backlighting is activated (step 138, shown by following icon "D" from the bottom of FIG. 5A to the top of FIG. 5B).

Upon activation of the start/stop button 46, the timer commences incrementing the current duration of event number 1 (as depicted in display condition 102 of FIG. 3), while monitoring for activation of either the start/stop button or the history button, and simultaneously monitoring the battery condition (steps 152 and 154). Step 140 depicts this operation.

If the start/stop button 46 is activated, step 142 initiates a series of steps involving activation of the "last" indicator (step 144); saving the duration of the most recent event in a history buffer (step 146); displaying the time of the most recent event on the small LCD display (step 148); and incrementing the current event counter (step 150). Flow then reverts to step 140 for continued incrementation of the duration of the current event in the large LCD display while monitoring the battery condition (steps 152 and 154) and monitoring for further activation of either the start/stop button or the history button.

Step 156 (following the "B" icon from FIG. 5B to FIG. 5C) commences the flow of operation upon activation of history button 48: the "last" indicator is deactivated (step 158); the "history" indicator is activated (step 160); the current event counter is checked (step 162); and the status of the history button (activated or not activated?) is monitored (step 164). If the history button remains activated, the LCD displays the preceding event number and duration (step 166), then monitors the condition of the start/stop button (activated or not)(step 168). If the start/stop button remains inactivated and the history button remains activated, the timer waits for any change in status of either key. If start/stop button 46 is activated, the temporary event counter is decremented (step 170) and tested (steps 172 and 174). If at some point the history button is no longer activated, step 164 changes the flow away from step 166 and moves to step 176, which involves resetting the current event counter, activates the "last" indicator (step 178), and deactivates the "history" indicator. Flow then reverts once more back to step 140 (following icon "A").

It may in some circumstances be desirable to include additional features to the basic "2 button" timer assembly 14 described in detail above, or in other circumstances to provide fewer features. In order to demonstrate alternative embodiments within the basic teachings of the present invention, following is a discussion of a "3 button" timer assembly and a "1 button" assembly.

Figure 6:
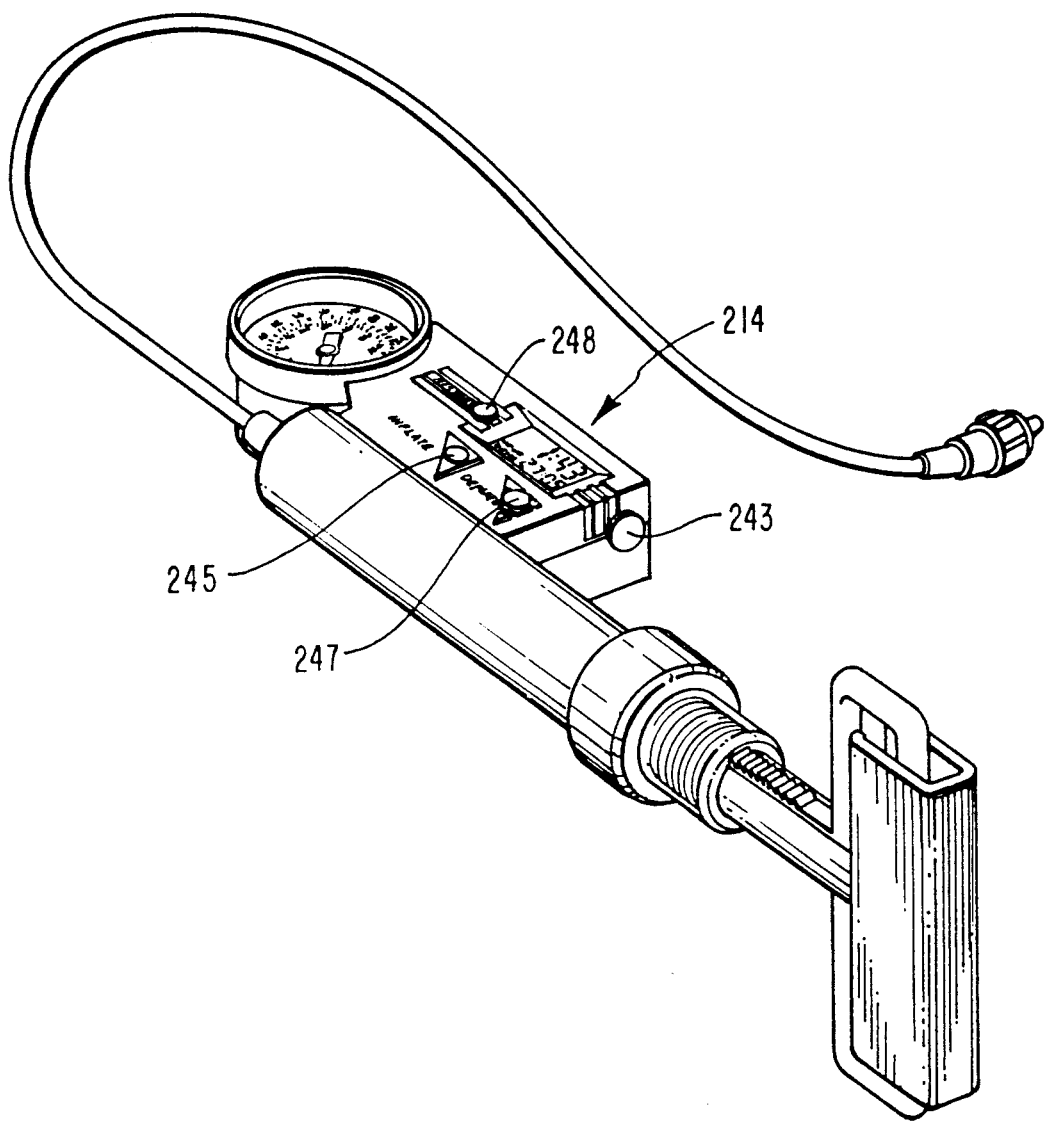
FIG. 6 is a perspective view of a second embodiment of the syringe apparatus of the present invention.

FIG. 6 depicts another presently preferred syringe apparatus in accordance with the present invention, this embodiment having a "3 button" timer assembly, shown generally by reference numeral 214. As with timer assembly 14, timer assembly 214 is advantageously provided with a "history" button 248. The "start/stop button" 46 of timer assembly 14, is replaced in timer assembly 214 by "inflate" button 245 and "deflate" button 247.

After applying battery power to the timer assembly 214 by actuating on/off button 243, the timer assembly may be activated by pressing inflate button 245. This starts timing of the first inflation event, and activates a label on the LCD screen indicating that the timer assembly is timing an inflation event. Timing continues until the syringe operator presses the deflate button 247.

As would be expected, pressing deflate button 247 resets the timer and commences timing of the first deflation event, and activates a label on the LCD display indicating that the timer assembly is timing a deflation event. The first inflation duration is saved to a buffer, which in the preferred embodiment will store up to 16 inflation and deflation events, although it will be appreciated that more or less buffer storage may be provided. Each subsequent activation of the inflate and deflate buttons moves the duration of the preceding event into the buffer, and commences timing of the current event. Each successive activation of the inflate or deflate button also increments a counter, which preferably is capable of incrementing up to 64 events.

In order to prevent errors such as consecutive "inflations", the timer is advantageously programmed so that the inflate button has no further effect during an inflation, and the deflate button has no effect during a deflation. Hence, pressing inflate button 245 during the course of an inflation event will be ignored by timer assembly 214. Likewise, pressing deflate button 247 during the course of a deflation will have no effect.

Historical information may be accessed through use of history button 248. While pressing and holding the history button, pressing either the inflate button or the deflate button scrolls back one event.

Figure 7:
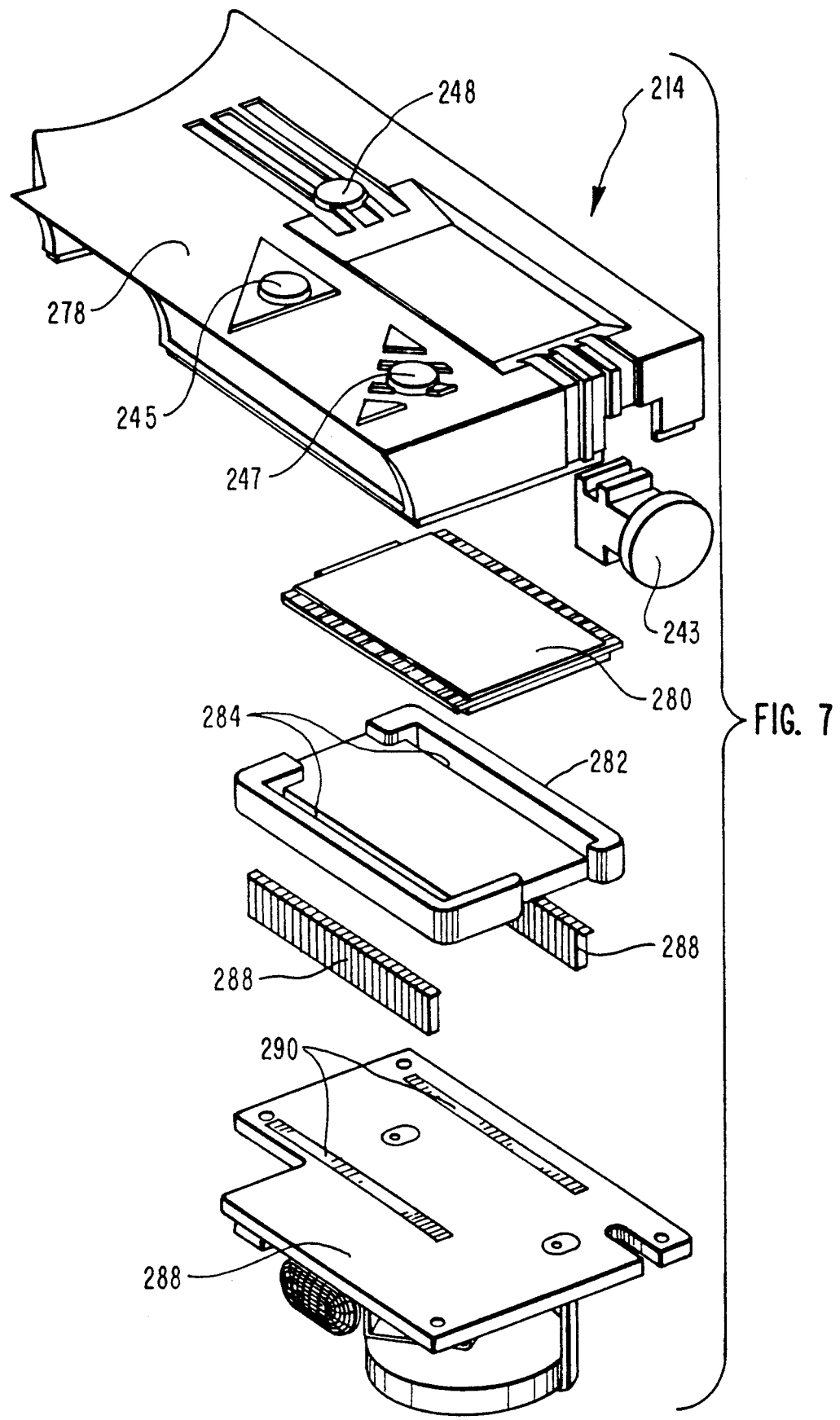
FIG. 7 is an exploded view of a portion of the timer assembly of the embodiment shown in FIG. 6.
Figure 8:
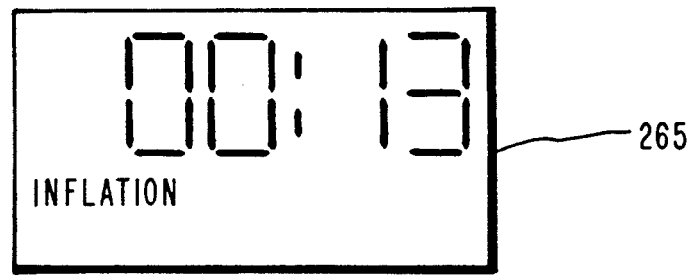
FIG. 8 is a series of views of the display of the three button timer assembly of FIG. 6 at various times during a fictitious use of that assembly.
Figure 8:
Figure 8:
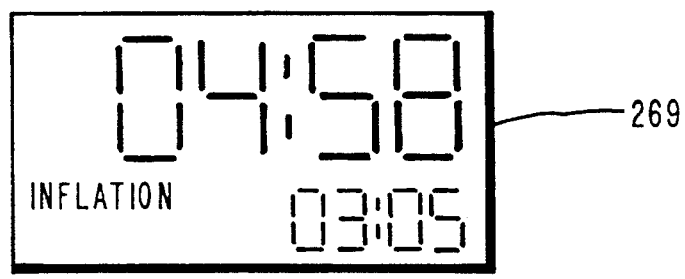

FIG. 8 illustrates several fictitious events using the 3 button timer assembly of FIG. 7. Display condition 265 illustrates an inflation event at a moment 13 seconds after it was initiated. It should be noted that the label "inflation" appears on the LCD display to indicate that an inflation is in process. By virtue of the fact that no information is displayed below the large numerals, a user will know that this is the first inflation event. Display condition 267 indicates a deflation event which has continued for 3 minutes, 5 seconds. The small numerals show that the preceding inflation event had a total duration of two minutes, 48 seconds. Display condition 269 depicts the next succeeding inflation event, indicating the current duration of deflation is 4 minutes, 58 seconds. The duration of the preceding deflation was 3 minutes, 5 seconds.

Figure 9:
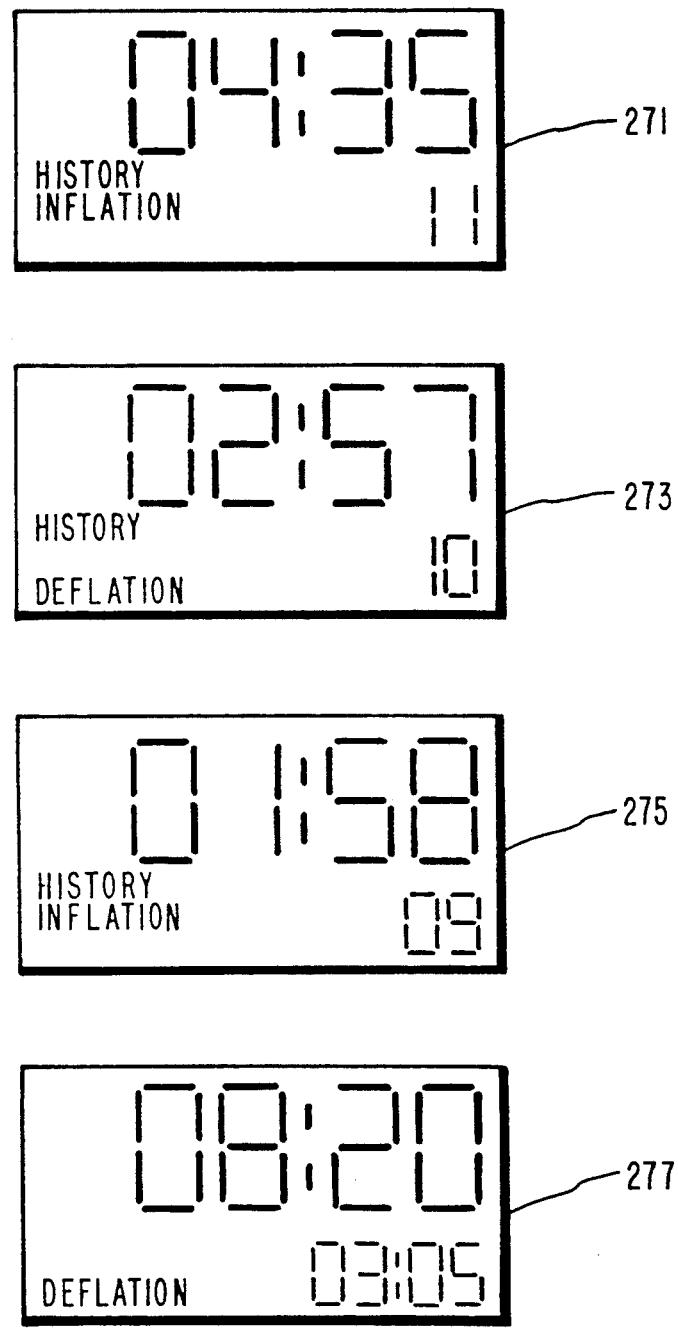
FIG. 9 is a series of views of the display of FIG. 8 showing how historical information may be viewed.

FIG. 9 illustrates the ability to review historical information. Upon pressing and holding the history button, the duration of the immediately past event is displayed. Display condition 271 indicates that event 11 was an inflation having a duration of 4 minutes, 35 seconds. Pressing either the inflate button 245 or deflate button 247, while continuing to hold history button 248, decrements the history buffer to the previous event. Thus, display condition 273 shows deflation event 10 had a duration of 2 minutes, 57 seconds. Pressing either the inflation or deflation button again results in display condition 275, which indicates that inflation event 9 had a duration of 1 minute, 58 seconds. Finally, releasing the history button returns the current event timer, as indicated at display condition 277, where the current deflation event has a current duration of 8 minutes, 20 seconds, and the duration of the preceding inflation event may be seen to have been 3 minutes, 5 seconds.

A presently preferred construction of a timer assembly in accordance with the present invention is illustrated in FIG. 7, which is an exploded view of a portion of timer assembly 214 of FIG. 6. Liquid crystal display 280 is shown immediately below top cover 278. The sides of LCD 280 are shown as comprising a series of electrical contacts which serve to activate the various segments of the display.

Below the LCD is a diffuser 282, which is preferably molded in a one piece structure from a generally transparent plastic. Diffuser 282 serves to backlight and support the LCD. Diffuser 282 has a pair of opposing slots which lie along the length of the LCD electrical contacts, thereby leaving those contacts exposed. Lying below diffuser 282 is an electronic timer module 288, which includes the electronic components of timer assembly 214 and the battery to operate them. A pair of electronic contact strips 290 lie along the surface of timer module 288, corresponding in position to the LCD electrical contacts.

Advantageously, from a manufacturing standpoint, a pair of "zebra" pads 288 are provided for placement between strips 290 and the LCD electrical contacts. Zebra pads 288 are constructed as a composite of small blocks of insulating material and conductive material, and are capable of carrying current from pads 290 to the LCD without mechanical connections. Zebra pads 288 extend through slots 284, and are held in place by the boundaries thereof.

Figure 10:
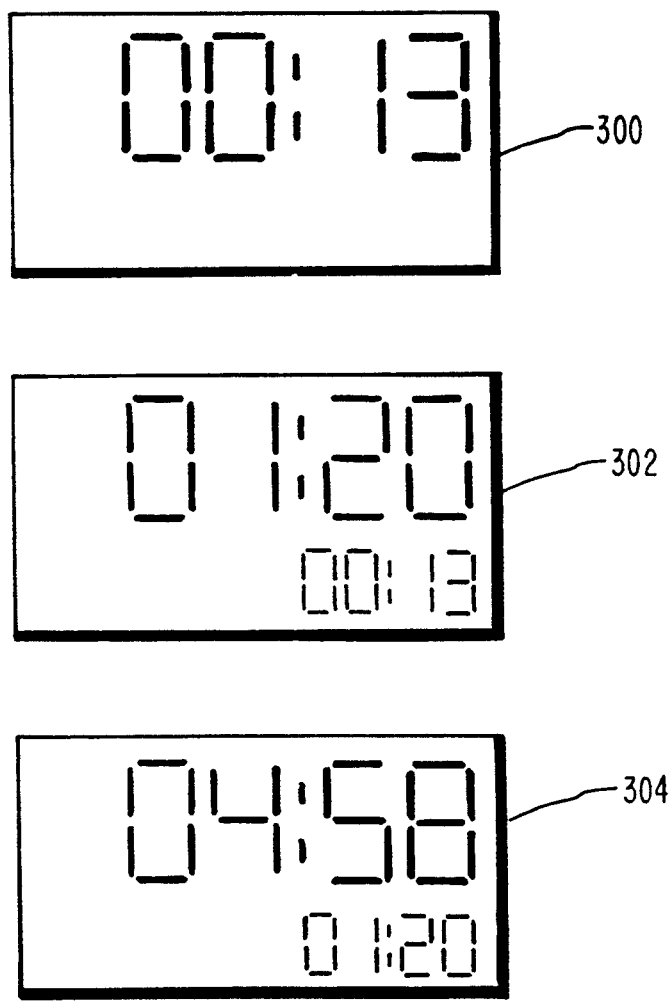
FIG. 10 is a series of views of a display which might be used in connection with a single button timer assembly.

As indicated above, it is also possible to provide a "1 button" timer assembly. Although not illustrated, the function of a 1 button embodiment will be readily understood from the disclosure set forth above. Unlike the 2 button and 3 button timer assemblies, it is currently contemplated that it might in some instances be less important to provide access to multiple historical events. Rather, it may be adequate in some circumstances to provide a timer assembly which shows the duration of the current event, and the duration of the immediately past event. These functions can be provided by a single button timer assembly, the single button being used to terminate timing of a current event, and commencing timing of the next succeeding event. Referring now to FIG. 10, display condition 300 illustrates a convenient display which might be used for a one button timer assembly. It shows an initial event having a total elapsed duration of 13 seconds. Upon activation of the control button, display condition 302 illustrates that the 13 second duration of that event will be displayed in small numerals on the LCD, while the large numerals depict the timing of the current event. Display condition 304, in turn shows a current elapsed time of 4 minutes, 58 seconds for the current event, and a historical duration of 1 minute, 20 seconds for the immediately past event.

It will be appreciated that the present invention may be embodied in other specific forms without departing from its spirit or essential characteristics. The described embodiments are to be considered in all respects only as illustrative and not restrictive, and the scope of the invention is indicated by the appended claims rather than by the foregoing description. All changes which come within the meaning and range of equivalency of the claims are to be embraced within their scope.

What is claimed and desired to be secured by United States Patent is:

1. An apparatus for use in inflating a balloon-tipped catheter, comprising:
   a syringe assembly capable of generating sufficient pressure to inflate a balloon-tipped catheter;
   a pressure gauge means attached to the syringe assembly having a pressure display for measuring and displaying the pressure generated by the syringe assembly; and
   a timer assembly attached to the syringe assembly for measuring durations of separate events of inflation and deflation of the balloon-tipped catheter, said timer assembly including:
    display means for visually displaying the duration of time which has passed since commencement of a current event of inflation or deflation and wherein the display means further includes a display showing the duration of the immediate past event of inflation or deflation; and
    first actuating means for commencing the timing of the duration of each successive event of inflation and deflation.

2. An apparatus as defined in claim 1, wherein the display showing the duration of the immediate past event of inflation or deflation further includes a display indicator labeling the display of the immediate past event of inflation or deflation as being a past event.

3. An apparatus as defined in claim 1 further display means further includes a display identifying the current event as being an inflation or a deflation.

4. An apparatus as defined in claim 1 further comprising:
    memory means for storing the duration of each event of inflation and deflation; and
    second actuating means for displaying the historical duration of each event of inflation and deflation.

5. An apparatus as defined in claim 4, wherein the duration and event number of the immediate past event of inflation or deflation is displayed by actuating the second actuating means, and wherein the duration and event numbers of additional past events are successively displayed by successive activations of the first actuating means.

6. An apparatus as defined in claim 4, wherein the first actuating means comprises separate means for commencing the timing of inflations and means for commencing the timing of deflations, and wherein the duration and event number of the immediate past event of inflation or deflation is displayed by actuating the second actuating means, and wherein the duration and event numbers of additional past events are successively displayed by successive activations of either of the means for commencing the timing of inflations or the means for commencing the timing of deflations.

7. An apparatus as defined in claim 4, wherein the first actuating means comprises a button which stops the timing of the current event and causes the total duration of that event to be stored in said memory means, and also starts the timing of the next succeeding event.

8. An apparatus as defined in claim 1 wherein the timer assembly display means is located in proximity to the pressure gauge display and is oriented so as to permit an operator of the syringe assembly to substantially simultaneously monitor the pressure within the syringe assembly and the data displayed on the timer assembly display means.

9. An apparatus as defined in claim 1 wherein the timer assembly first actuating means is located at a position in proximity with the timer assembly display means and the pressure gauge display, so as to permit an operator of the syringe assembly to easily actuate such actuating means while substantially simultaneously monitoring the pressure gauge display and the timer assembly display.

10. An apparatus as defined in claim 1, wherein the display is a liquid crystal display having a series of electrical contacts along the sides thereof, and wherein a pair of zebra strips is used to complete an electrical contact between the liquid crystal display and electronic timing means.

11. A syringe apparatus for use in inflating a balloon-tipped catheter, comprising:
    a syringe assembly capable of generating sufficient pressure to inflate a balloon-tipped catheter;
    a pressure gauge means attached to the syringe assembly having a pressure display for measuring and displaying the pressure generated by the syringe assembly;
    a timer assembly attached to the syringe assembly for measuring durations of separate events of inflation and deflation of the balloon-tipped catheter, said timer assembly including:
        display means for visually displaying the duration of time which has passed since commencement of a current event of inflation or deflation and the duration of the immediate past event of inflation or deflation;
        first actuating means for commencing the timing of the duration of each successive event of inflation and deflation;
        memory means for storing the duration of each event of inflation and deflation;
        second actuating means for displaying the duration of prior events of inflation and deflation; and
        indicator means for labeling the display of an immediate past event of inflation or deflation as being a past event when the second actuating means is actuated, and for labeling the event number of past events when the second actuating means is actuated.

12. An apparatus as defined in claim 11 wherein the timer assembly display means is located in proximity to the pressure gauge display and is oriented so as to permit an operator of the syringe assembly to substantially simultaneously monitor the pressure within the syringe assembly and the data displayed on the timer assembly display means.

13. An apparatus as defined in claim 11 wherein the timer assembly first actuating means is located at a position in proximity with the timer assembly display means and the pressure gauge display, so as to permit an operator of the syringe assembly to easily actuate such actuating means while substantially simultaneously monitoring the pressure gauge display and the timer assembly display.

14. An apparatus as defined in claim 11 wherein the first actuating means comprises a start/stop button which functions to terminate the timing of an event of inflation or deflation and also to commence the timing of a successive event of inflation or deflation.

15. An apparatus as defined in claim 11 wherein the first actuating means comprises a first button for commencing the timing of inflation events, and a second button for commencing the timing of deflation events, each of said first and second buttons also serving to terminate the timing of a previous event of deflation or inflation.

16. An apparatus as defined in claim 15, wherein the first button serves to terminate the timing of a deflation event and commence the timing of an inflation event, but has no function if the current event is an inflation event; and wherein the second button serves to terminate the timing of an inflation event and commence the timing of a deflation event, but has no function if the current event is a deflation event.

17. An apparatus for use in inflating a balloon-tipped catheter, comprising:
- a syringe assembly capable of generating sufficient pressure to inflate a balloon-tipped catheter;
- a pressure gauge means attached to the syringe assembly having a pressure display for measuring and displaying the pressure generated by the syringe assembly; and
- a timer assembly attached to the syringe assembly for measuring durations of separate events of inflation and deflation of the balloon-tipped catheter, said timer assembly including:
    - display means for visually displaying the duration of time which has passed since commencement of a current event of inflation or deflation and wherein the display means further includes a display identifying the current event as being an inflation or a deflation; and
    - first actuating means for commencing the timing of the duration of each successive event of inflation and deflation.

18. An apparatus for use in inflating a balloon-tipped catheter, comprising:
- a syringe assembly capable of generating sufficient pressure to inflate a balloon-tipped catheter;
- a pressure gauge means attached to the syringe assembly having a pressure display for measuring and displaying the pressure generated by the syringe assembly; and
- a timer assembly attached to the syringe assembly for measuring durations of separate events of inflation and deflation of the balloon-tipped catheter, said timer assembly including:
    - display means for visually displaying the duration of time which has passed since commencement of a current event of inflation or deflation;
    - first actuating means for commencing the timing of the duration of each successive event of inflation and deflation;
    - memory means for storing the duration of each event of inflation and deflation; and
    - second actuating means for displaying the historical duration of each event of inflation and deflation.

* * * * *

UNITED STATES PATENT AND TRADEMARK OFFICE
CERTIFICATE OF CORRECTION

PATENT NO. : 5,259,838
DATED : November 9, 1993
INVENTOR(S) : STEVEN R. TAYLOR et al.

It is certified that error appears in the above-indentified patent and that said Letters Patent is hereby corrected as shown below:

```
    Column 3, line 45, after ";" the next sentence should
begin a new paragraph on the following line
    Column 4, line 58, delete "being" and insert --is--
    Column 4, line 62, delete "being" and insert --is--
    Column 6, line 45, before "of" insert --As the start/stop
button is activated at the commencement--
    Column 11, line 18, claim 3, delete "further" and insert
--wherein the--
```

Signed and Sealed this

Fourth Day of October, 1994

Attest:

BRUCE LEHMAN

Attesting Officer

Commissioner of Patents and Trademarks